United States Patent [19]

Niederer et al.

[11] Patent Number: 4,892,548

[45] Date of Patent: Jan. 9, 1990

[54] JOINT SOCKET

[75] Inventors: Gino Niederer, Zollikofen; Otto Frey, Winterthur, both of Switzerland

[73] Assignees: Gebruder Sulzer, Winterthur; Protek AG, Bern, both of Switzerland

[21] Appl. No.: 454,993

[22] Filed: Jan. 3, 1983

[30] Foreign Application Priority Data

Jan. 12, 1982 [CH] Switzerland .......................... 147/82

[51] Int. Cl.⁴ ............................................... A61F 2/34
[52] U.S. Cl. ........................................ 623/22; 623/66
[58] Field of Search ................... 3/1, 1.9, 1.91, 1.912, 3/1.913; 128/92 C, 92 CA

[56] References Cited

U.S. PATENT DOCUMENTS 3,806,960  4/1974  Weber ................................. 3/1.913
4,123,806  11/1978 Amustutz et al. ................... 3/1.912
4,224,698  9/1980  Hopson ............................... 3/1.912

Primary Examiner—Richard J. Apley
Assistant Examiner—David J. Isabella
Attorney, Agent, or Firm—Kenyon & Kenyon

[57] ABSTRACT

The external surface of the hip joint socket is provided with a contrast ring in a diametric plane of the joint head receiving cavity as well as with a metallic measuring ring in the upper surface of the socket body. The measuring ring is concentric to the axis of rotation of the body and is parallel to the plane of the contrast ring. By measuring the distance of the two metallic rings from each other in an X-ray picture, a determination can be made as to whether a displacement of the center of the spherical joint head is due in part to a cold flow of the socket material or exclusively to abrasion.

6 Claims, 1 Drawing Sheet

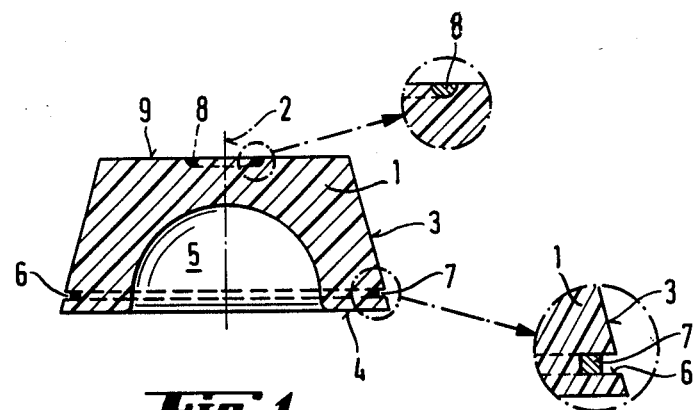
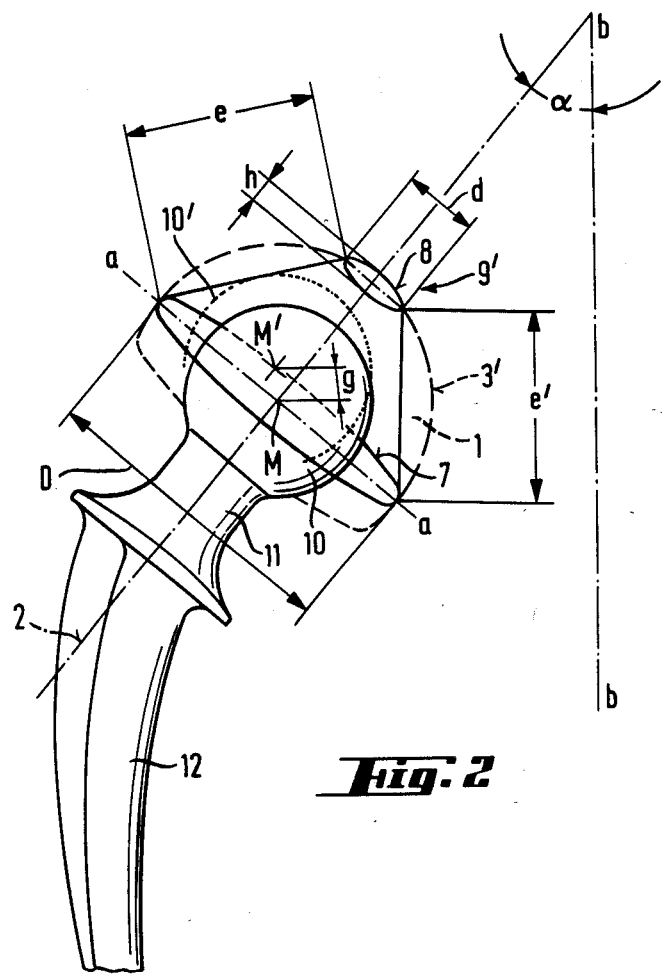

JOINT SOCKET

This invention relates to a joint socket for receiving a spherical joint head of a hip joint prosthesis.

As is known, artificial hip joint sockets in which a spherical head of a hip joint prosthesis is supported within a hemispherical cavity often consist of plastic, especially polyethylene, or a ceramic material, for example aluminum oxide. In order to improve the visibility of the socket in an X-ray picture, a metal wire ring is usually inserted in an external surface of the socket, generally near the open edge of the hemispherical cavity, in order to form a contrast ring.

If relative displacements of the spherical head in the joint socket or relative displacements to the contrast ring are observed by comparison of X-ray photographs which are taken immediately after implantation and after one or several years, these changes of position may have two causes. First, a cold flow, i.e. an irreversible plastic deformation, may have occurred inside the socket cavity. Second, the relative displacement may have been caused by abrasion. Of course, such a change of position may be caused partly by a cold flow and partly by abrasion.

Generally, since a cold flow of the socket material produces no or only slight physiological effects, while abrasion in excess of the normal amount, i.e. of about 0.1 millimeter per year, is critical in the long run, it is desirable to be able to recognize the cause of a relative displacement of the spherical head in the joint socket appearing in an X-ray picture.

Accordingly, it is an object of the invention to provide a joint socket for a hip joint prosthesis which permits relative displacements to be determined from comparing X-ray pictures taken at different time periods.

It is another object of the invention to be able to determine whether a change of the relative position of a spherical head of a hip joint prosthesis in a joint socket has been caused mainly by cold flow or primarily by abrasion.

Briefly, the invention provides a joint socket for receiving a spherical joint head of a hip joint prosthesis which is formed of a non-metallic body, a metallic contrast ring and a metal measuring ring.

The non-metallic body is formed with an external surface which is at least partly a surface of revolution about a longitudinal axis as well as an internal hemispherical cavity for receiving a spherical joint head.

The metallic contrast ring is disposed in the external surface of the body concentric to the axis of the body and, preferably, in a diametric plane of the hemispherical cavity i.e. the equatorial plane of the socket.

The metal measuring ring is fixed in the external surface concentric to the axis of the body and parallel to the contrast ring. The metal measuring is of known diameter and is located at a given vertical distance from the plane of the contrast ring.

A cold flow displacement can be recognized from subsequently taken X-ray pictures by comparing the distance between the two major axes of the ellipses formed by the contrast ring and measuring ring on the X-ray pictures. If the distances on the left and right of the photograph ellipse images are the same, there is no cold flow of the socket material. However, if these two distances are different, this indicates that a cold flow has taken place.

In addition to the above, the use of the measuring ring with the contrast ring offers a further advantage in that the position of an implanted joint socket in a pelvis bone can be checked. In particular, one can determine the inclination of the socket, i.e. the angle of inclination between the socket axis and the body axis. This angle of inclination should be about 40° to 45°. In addition, the anteversion of the socket can be determined. This angle is optimally 12°. The inclination is, as is known, the slope of the joint socket, i.e. for example of an edge plane, against the horizontal or the slope of the socket axis against the vertical body axis. Anteversion is a rotation of the socket about the diametric axis, situated in the frontal plane of the body, of the edge plane in a sagittal direction forward.

In order to make the distance between the two metal rings as large as possible to thereby increase the relative measurement precision in measuring a distance, the measuring ring is arranged in the summit region of the external surface of the socket body i.e. an area opposite the socket end face. Further, the contrast ring is located in the diametric plane of the hemispherical cavity of the socket body to expedite the determination of the desired center of the spherical head.

The two rings may be made of any metal or metal alloy which is customarily used in implant technology. However, the joint socket is made primarily of plastic, particularly of polyethylene of the classification HDPE or UHMW.

These and other objects and advantages of the invention will become more apparent from the following detailed description taken in conjunction with the accompanying drawings wherein:

FIG. 1 illustrates a cross-sectional view of a joint socket constructed in accordance with the invention; and FIG. 2 illustrates a view of an implanted prosthesis as appearing in an X-ray picture taken in the sagittal direction.

Referring to FIG. 1, the joint socket has a nonmetallic body 1 with an external surface at least partly of a surface of revolution, i.e. the body has a truncated conical external surface 3 about a longitudinal axis of rotation 2. In addition, the body 1 has an internal hemispherical cavity 5 extended at the base 4 which is disposed about the axis of rotation 2 in concentric relation with the external surface 3.

As shown, the non-metallic body 1 has a circumferential groove in the external surface 3 near the base 4 in which a metallic contrast ring 7 is positioned. As illustrated, the contrast ring 7 is disposed in an equatorial plane of the cavity 5.

The joint socket also has a metal measuring ring 8 in a flat end face 9 of the body 1 i.e. in an area opposite the cavity 5. This metal measuring ring 8 has a known diameter and is concentric with the external surface 3 being coaxial with the axis of rotation 2 while being parallel to the contrast ring 7 and spaced from the cavity 5.

Referring to FIG. 2, the socket may be formed with a hemispherical external surface 3', as indicated in broken lines, in which case, the metal measuring ring 8 is arranged in the summit region 9' of the surface 3'. As indicated, the socket body 1 receives a spherical joint head 10 which is mounted on a neck 11 of a prosthesis shank 12.

The distance of the measuring ring 8 from the contrast ring 7 and, hence, the circumference of the measuring ring 8 are selectable at will. However, the distance of the measuring ring 8 from the contrast ring 7 should not be so great that the measuring ring 8 does not lie in the shadow region of the spherical head 10 in an X-ray photograph.

Generally, a hip joint prosthesis is in a position corresponding to the solid line position indicated in FIG. 2 immediately after implantation. Further, due to anteversion in the body and, hence, in an X-ray picture taken in the sagittal direction, the joint socket which is indicated in broken lines, takes up a position in which the contrast ring 7 and measuring ring 8 appear as narrow ellipses.

In order to determine the angle of inclination, a determination is first made of the direction of the major ellipse axis aa of the contrast ring 7 with the aid of the largest diameter D thereof present in the X-ray picture. The perpendicular to this axis aa forms an angle of inclination $\alpha$ with the axis bb of the body.

The anteversion angle can be determined by measuring the axes d and h of the measuring ring 8 which appears as an ellipse in the X-ray picture. The greater the axis h is relative to the axis d, the greater is the anteversion of the joint socket.

FIG. 2 as shown in dotted lines illustrates a position, assumed as an example, of the contour 10' of the spherical head 10 in a later X-ray photograph taken some time after implantation. The displacement g of the center M' which occurred in the time interval between the two photographs as compared with the original or desired center M of the spherical head 10 can be determined as follows.

First, the major half-axes D,d of the two "ellipses" of the rings 7, 8 are measured and halved. The shortest, i.e. the perpendicular, connection of the two axes centers establishes the axis of rotation 2 for the joint socket. The intersection of the axis of rotation 2 with the major half-axis aa of the contrast ring 7 has a defined distance, different depending on the type socket, from the desired center M of the spherical head 10 after implantation. In the example shown, the intersection and the desired center of the spherical head 10 coincide, i.e. the distance is 0. The center M' of the spherical head 10' in the changed position is obtained from the largest dimension of the spherical head picture, giving the diameter of the head 10' on which M' is in the center. The shortest distance M—M' is the sought displacement g.

The displacement g of the spherical head 10 which is shown greatly exaggerated in FIG. 2 may have been caused by a cold flow and/or abrasion.

Cold flow can be recognized from the X-ray picture by comparing the distances e and e', respectively, between the two major axes D and d of the two "ellipses" of the contrast ring 7 and of the measuring ring 8 on the left side and on the right side. If the two distances e, e' on the left and right are the same, there is no cold flow of the socket material. However, these distances are different on the left and right as soon as a cold flow of the material has taken place.

Hence, when a displacement g is found, it can be determined whether the displacement was caused by abrasion alone or at least in part by cold flow of the material.

The invention thus provides a joint socket which can be implanted in a pelvis bone for a hip joint prosthesis with means which can be used to determine changes in relative displacement of the socket.

What is claimed is:

1. A joint socket for receiving a spherical joint head of a hip joint prosthesis, said socket having a non-metallic body with an external surface at least partly of a surface of revolution about a longitudinal axis and an internal hemispherical cavity;
   a metallic contrast ring in said surface of said body concentric to said axis; and
   a metal measuring ring fixed in said surface in an area opposite and spaced from said cavity and concentric to said axis, said measuring ring being longitudinally spaced from and parallel to said contrast ring wherein the spacing of said measuring ring from said contrast ring is so great that said measuring ring does not lie in the shadow region of a spherical joint head in an X-ray photograph.

2. A joint socket as set forth in claim 1 wherein said contrast ring is disposed in a diametric plane of said cavity.

3. A joint socket as set forth in claim 1 wherein said body has a hemispherical external surface.

4. A joint socket as set forth in claim 4 wherein said contract ring is disposed in a an equatorial plane of said cavity.

5. A joint socket as set forth in claim 1 wherein said body has a conical external surface and a flat end face and said measuring ring is disposed in said flat end face.

6. A joint socket as set forth in claim 5 wherein said contrast ring is disposed in an equatorial plane of said cavity.

* * * * *